Sept. 12, 1961 P. DOT Plant Pat. 2,091
ROSE PLANT
Filed Nov. 22, 1960
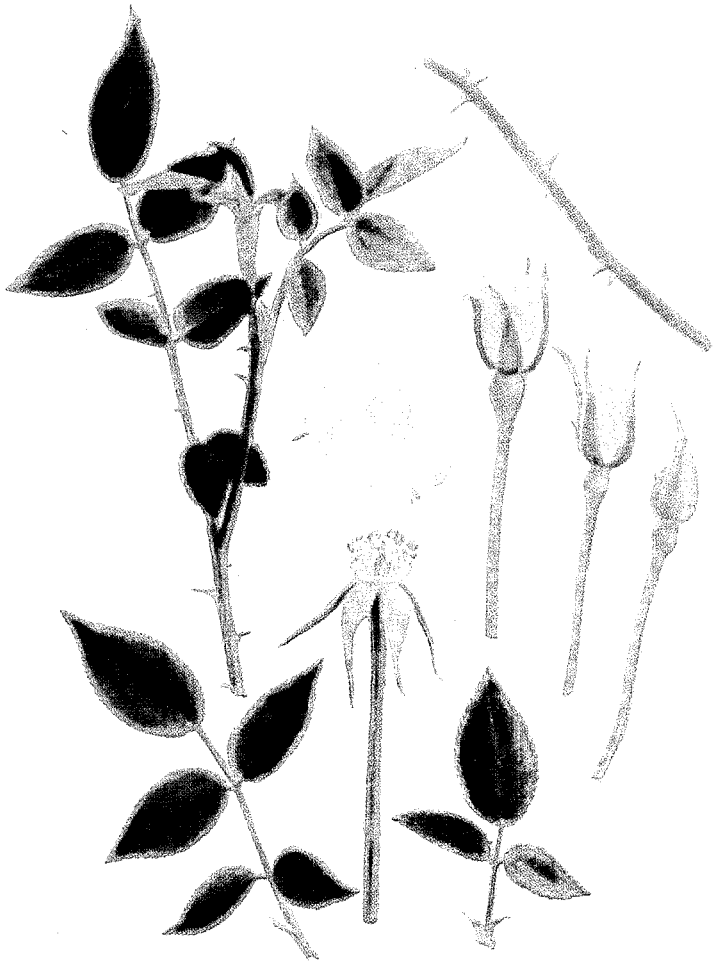
Inventor.
Pedro Dot
By: Robb & Robb
Attorneys.

United States Patent Office

Plant Pat. 2,091
Patented Sept. 12, 1961

2,091
ROSE PLANT

Pedro Dot, Barcelona, Spain, assignor to The Conard-Pyle Company, West Grove, Pa., a corporation of Pennsylvania Filed Nov. 22, 1960, Ser. No. 71,108
1 Claim. (Cl. 47—61)

The present invention relates to a new and distinct variety of rose plant of the miniature class, which was originated by me by crossing the variety "Perla de Montserrat" (unpatented) with an unnamed and unpatented seedling of "Rosina" (unpatented) × "Eduardo Toda" (unpatented).

The primary objective of this breeding was to produce a new rose variety of the miniature class, having an improved plant habit and superior floriferousness as compared with previously known varieties of yellow miniature roses and presently available in commerce. This objective was fully achieved, along with other desirable improvements as evidenced by the following unique combination of characteristics which are outstanding in the new variety and which distinguish it from its parents, as well as from all other varieties of which I am aware:

(1) A low-growing compact habit of growth;

(2) Superior floriferousness in comparison with such varieties as "Baby Gold Star" (Plant Patent No. 407) and "Rosina" (unpatented);

(3) Attractive blooms of miniature size, ranging from 1¼ to 1½ inches in diameter;

(4) A distinctive Mimosa Yellow general color tonality of the blooms; and (5) Ease of propagation by cuttings.

Asexual reproduction of the new variety by own-root cuttings, as performed at West Grove, Pennsylvania, U.S.A., shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with the Horticultural Colour Chart of the Royal Horticultural Society (hereinafter abbreviated as "HCC") and Nickerson Color Fan (hereinafter abbreviated as "Nickerson"), except where general color terms of ordinary dictionary significance are obvious:

Type: Hardy; dwarf; outdoor; seedling; for garden decoration.

Class: Miniature.

Breeding: Seedling.

*Seed parent.*—"Perla de Montserrat."

*Pollen parent.*—An unnamed seedling of "Rosina" × "Eduardo Toda."

Propagation: Holds its distinguishing characteristics through succeeding propagations by cuttings.

*Flower*

Locality where grown and observed: West Grove, Pennsylvania, U.S.A.

Flowers borne: Usually singly to stem; on short stems of normal strength.

Quantity of bloom: Free, outdoors.

Continuity: Continuous.

Fragrance: Very slight.

Bud:

*Peduncle.*—Short; slender; erect; rough; numerous green hairs. Color—between Strong Yellow Green, Plate 7.5GY 6/8 (Nickerson) and Strong Yellow Green, Plate 5GY 6/8 (Nickerson).

*Before calyx breaks.*—Size—small. Form—short; pointed; with a conspicuous neck; with foliaceous appendages on the surface of the bud; with slender bristle-like foliaceous parts extending beyond the tip of the bud equal to ¼ or more of its length.

*As calyx breaks.*—Color—Brilliant Yellow, Plate 5Y 9/9 (Nickerson), lightly washed with Strong Yellowish Pink, Plate 10R 7/9 (Nickerson).

*As first petal opens.*—Size—small. Form—short; infondibular. Color: outside—Barium Yellow, Plate 503/1 (HCC), shading to Barium Yellow, Plate 503 (HCC) at base of petal; inside—Mimosa Yellow, Plate 602/1 (HCC), shading to Mimosa Yellow, Plate 602 (HCC) at base of petal.

*Opening.*—Opens up well.

Bloom:

*Size (when fully open).*—Small; from 1¼ inches to 1½ inches.

*Petalage.*—Semi-double; from 10 to 12 petals; arranged irregularly.

*Form.*—Cupped at first, but becoming open; petals at first being loosely rolled outward, and remaining loosely rolled outward at maturity.

Petals:

*Texture.*—Thin.

*Appearance.*—Inside—satiny. Outside—shiny.

*Shape.*—Outer petals—obovate. Inner petals—irregular.

This description of a newly opened flower was made from a rose grown in greenhouse during the month of June at West Grove, Pennsylvania, U.S.A.:

*Color.*—Outer petal: outside surface—Barium Yellow, Plate 503/1 (HCC), shading to Barium Yellow, Plate 503 (HCC) at base of petal; inside surface—Mimosa Yellow, Plate 602/1 (HCC), shading to Mimosa Yellow, Plate 602 (HCC) at base of petal. Inner petal: outside surface—Barium Yellow, Plate 503/1 (HCC), shading to Barium Yellow, Plate 503 (HCC) at base of petal, and often lightly washed with Moderate Pink, Plate 10RP 8/5 (Nickerson); inside surface—Mimosa Yellow, Plate 602/1 (HCC), shading to Mimosa Yellow, Plate 602 (HCC) at base of petal.

This description was made from a rose that was open for three days in a greenhouse during the month of June at West Grove, Pennsylvania, U.S.A.:

*Color.*—Outer petal: outside surface—slightly lighter than Mimosa Yellow, Plate 602/3 (HCC), grading to Mimosa Yellow, Plate 602/2 (HCC) at base of petal; inside surface—slightly lighter than Mimosa Yellow, Plate 602/3 (HCC), grading to Mimosa Yellow, Plate 602/1 (HCC) over the basal quarter of the petal. Inner petal: outside surface—slightly lighter than Mimosa Yellow, Plate 602/3 (HCC), grading to Mimosa Yellow, Plate 602/1 (HCC) at base of petal; inside surface—slightly lighter than Mimosa Yellow, Plate 602/3 (HCC), grading to Mimosa Yellow, Plate 602/1 (HCC) over base of petal.

*General color effect.*—Newly opened flower—Mimosa Yellow, Plate 601/1 (HCC). Three days open—varying from slightly lighter than Mimosa Yellow, Plate 602/3 (HCC) to Mimosa Yellow, Plate 602/1 (HCC).

*Behaviour.*—Drop off cleanly.

*Flower longevity.*—On bush in garden—3 or more days in June. Cut roses grown in greenhouse and kept at living room temperatures—3 or more days in June.

*Reproductive organs*

Stamens: Medium number; arranged irregularly about pistils.
Filaments: Most with anthers; short. Color—Primrose Yellow, Plate 601/2 (HCC).
Anthers: All open at once; small; occasionally an anther fused with a petaloid. Color—Mimosa Yellow, Plate 602/2 (HCC).
Pollen: Sparse. Color—yellow.
Pistils: Few.
Styles: Uneven; short; thin; bunched.
Stigma: Color—red.
Ovaries: All enclosed in receptacle.
Hips: None observed.
Sepals: Permanent; short; spear-shaped.
Seeds: None observed.

*Plant*

Foliage:
*Leaves.*—Compound of 5 or sometimes 7 leaflets; normal abundance; very small; thin.
*Leaflets.* — Shape — oval but sometimes ovoid. Apex—acute. Base—obtuse. Margin—simply serrate.
*Color.* — Mature: upper surface — near Spinach Green, Plate 0960 (HCC); under surface—near Lavender Green, Plate 000761 (HCC). Young: upper surface—Lettuce Green, Plate 861 (HCC), with a thin margin of Garnet Brown, Plate 00918/3 (HCC); under surface—near Willow Green, Plate 000862 (HCC).

*Rachis (the supporting stem of the compound leaf).* — Light. Upper side — grooved; hairy. Under side—sparsely prickly.
*Stipules.*—Very short; very narrow; with very short points turning out at an angle of about 45°.
*Disease resistance.*—Comparable to that of the average variety grown under the same cultural conditions at West Grove, Pennsylvania, U.S.A.

Growth:
*Habit.*—Dwarf; bushy; much-branched.
*Growth.*—Free.
*Canes.*—Very light.
*Main stems.*—Bright. Color—slightly darker than Lettuce Green, Plate 861 (HCC). Prickles—several; color—near Strong Yellow Green, Plate 5GY 7/10 (Nickerson). Hairs—none.
*Branches.*—Bright. Color—slightly darker than Lettuce Green, Plate 861 (HCC). Prickles—several; color—near Strong Yellow Green, Plate 5GY 7/10 (Nickerson). Hairs—none.
*New shoots.*—Bright. Color—Lettuce Green, Plate 861 (HCC). Prickles — several; color — near Strong Yellow Green, Plate 5GY 7/10 (Nickerson), with base overlaid with Deep Pink, Plate 2.5R 6/11 (Nickerson). Hairs—none.

I claim:

A new and distinct variety of rose plant of the miniature class, substantially as herein shown and described, characterized particularly as to novelty by the unique combination of a low-growing compact habit of growth, superior floriferousness, attractive blooms of miniature size, a distinctive Mimosa Yellow general color tonality of the blooms, and ease of propagation by cuttings.

No references cited.